United States Patent
Shimon et al.

(10) Patent No.: US 8,062,324 B2
(45) Date of Patent: Nov. 22, 2011

(54) DEVICE AND METHOD FOR VASCULAR FILTER

(75) Inventors: Dov V. Shimon, Herzlia-Pituach (IL); Gil Naor, Ramat Hasharon (IL); Yuval Shezifi, Haifa (IL)

(73) Assignee: S.M.T. Research and Development Ltd., Herzliya Pituach (IL)

( * ) Notice: Subject to any disclaimer, the term of this patent is extended or adjusted under 35 U.S.C. 154(b) by 911 days.

(21) Appl. No.: 11/429,443

(22) Filed: May 8, 2006

(65) Prior Publication Data
US 2007/0270901 A1 Nov. 22, 2007

(51) Int. Cl.
*A61M 29/00* (2006.01)
(52) U.S. Cl. ............................................ 606/200
(58) Field of Classification Search .......... 606/200, 606/195; 604/103.06, 103.07, 104, 532
See application file for complete search history.

(56) References Cited

U.S. PATENT DOCUMENTS

| | | | |
|---|---|---|---|
| 5,417,708 A * | 5/1995 | Hall et al. ................. | 606/200 |
| 5,576,367 A | 11/1996 | O'Brien et al. | |
| 5,601,595 A * | 2/1997 | Smith ....................... | 606/200 |
| 5,807,330 A | 9/1998 | Teitelbaum | |
| 5,941,896 A | 8/1999 | Kerr | |
| 5,951,599 A | 9/1999 | McCrory | |
| 6,042,598 A | 3/2000 | Tsugita et al. | |
| 6,093,199 A * | 7/2000 | Brown et al. .............. | 606/200 |
| 6,139,517 A * | 10/2000 | Macoviak et al. ......... | 604/8 |
| 6,146,370 A | 11/2000 | Barbut | |
| 6,258,120 B1 * | 7/2001 | McKenzie et al. ......... | 623/1.36 |
| 6,371,935 B1 * | 4/2002 | Macoviak et al. ......... | 604/43 |
| 6,395,014 B1 * | 5/2002 | Macoviak et al. ......... | 606/200 |
| 6,419,686 B1 * | 7/2002 | McLeod et al. ............ | 606/200 |
| 6,499,487 B1 * | 12/2002 | McKenzie et al. ......... | 128/898 |
| 6,626,886 B1 | 9/2003 | Barbutt | |
| 6,656,204 B2 | 12/2003 | Ambrisco et al. | |
| 6,673,089 B1 | 1/2004 | Yassour et al. | |
| 6,675,696 B1 | 1/2004 | Marotta et al. | |
| 6,712,834 B2 | 3/2004 | Yassour et al. | |
| 6,723,116 B2 * | 4/2004 | Taheri ...................... | 623/1.11 |
| 6,740,112 B2 | 5/2004 | Yodfat et al. | |
| 6,866,680 B2 | 3/2005 | Yassour et al. | |
| 6,899,729 B1 | 5/2005 | Cox et al. | |
| 6,953,438 B2 | 10/2005 | Milo | |
| 7,122,043 B2 | 10/2006 | Greenhalgh et al. | |
| 7,144,421 B2 * | 12/2006 | Carpenter et al. ......... | 623/1.31 |
| 2002/0077596 A1 * | 6/2002 | McKenzie et al. ......... | 604/104 |
| 2002/0091354 A1 * | 7/2002 | Navia et al. ............... | 604/96.01 |
| 2002/0143362 A1 * | 10/2002 | Macoviak et al. ......... | 606/200 |
| 2003/0158574 A1 * | 8/2003 | Esch et al. ................. | 606/200 |
| 2003/0171803 A1 * | 9/2003 | Shimon ..................... | 623/1.24 |
| 2004/0073253 A1 * | 4/2004 | Morrill et al. .............. | 606/200 |
| 2004/0215167 A1 | 10/2004 | Belson | |

(Continued)

OTHER PUBLICATIONS

International Search Report for International Application No. PCT/IL07/00557. Date of mailing Sep. 10, 2008.

*Primary Examiner* — Gary Jackson
*Assistant Examiner* — Erin Colello
(74) *Attorney, Agent, or Firm* — Clark & Elbing LLP (57) ABSTRACT

A device implantable into a blood vessel having a filter to prevent particles from passing into a blood vessel, and having bows extending from a horizontal plain of the device, such bows to hold such device in place in a blood vessel.

25 Claims, 5 Drawing Sheets

U.S. PATENT DOCUMENTS

| | | |
|---|---|---|
| 2005/0137696 A1* | 6/2005 | Salahieh et al. .............. 623/2.11 |
| 2006/0009798 A1* | 1/2006 | Callister et al. ............... 606/200 |
| 2006/0009799 A1* | 1/2006 | Kleshinski et al. ........... 606/200 |
| 2006/0015138 A1* | 1/2006 | Gertner ......................... 606/200 |
| 2006/0161241 A1* | 7/2006 | Barbut et al. ................. 623/1.15 |
| 2008/0065145 A1 | 3/2008 | Carpenter |

\* cited by examiner

DEVICE AND METHOD FOR VASCULAR FILTER

FIELD OF THE INVENTION

Embodiments of the invention relate to devices that are inserted in a blood vessel or other body lumen, and in particular to a filter that may block particles from entering a blood vessel.

BACKGROUND OF THE INVENTION

Particles such as emboli may form, for example, as a result of the presence of particulate matter in the bloodstream. Particulate matter may originate from for example a blood clot occurring in the heart. The particulate may be a foreign body, but may also be derived from body tissues. For example, atherosclerosis, or hardening of the blood vessels from fatty and calcified deposits, may cause particulate emboli to form. Moreover, clots can form on the luminal surface of the atheroma, as platelets, fibrin, red blood cells and activated clotting factors may adhere to the surface of blood vessels to form a clot.

Blood clots or thrombi may also form in the veins of subjects who are immobilized, particularly in the legs of bedridden or other immobilized patients. These clots may then travel in the bloodstream, potentially to the arteries of the lungs, leading to a common, often-deadly disease called pulmonary embolus. Thrombus formation, and subsequent movement to form an embolus, may occur in the heart or other parts of the arterial system, causing acute reduction of blood supply and hence ischemia. The ischemic damage often leads to tissue necrosis of organs such as the kidneys, retina, bowel, heart, limbs, brain or other organs, or even death. Since emboli are typically particulate in nature, various types of filters have been proposed in an attempt to remove or divert such particles from the bloodstream before they can cause damage to bodily tissues.

SUMMARY OF THE INVENTION

Some embodiments of the invention include an intra-vascular device having a filter to prevent a particle in a blood vessel from passing through the filter, a skeleton to hold the filter, and more than one bow extending outwards from a horizontal plane of the device, and wherein a lateral surface of the lower of the more than one bow is in contact with a surface of a first blood vessel, and a lateral surface of the upper of the more than one bow is in contact with a surface of a second blood vessel. In some embodiments, the surface of the first blood vessel is a lateral surface of an ascending aorta, and a surface of the second vessel is a medial surface of a subclavean artery.

In some embodiments, an end of the skeleton is to bend below a plane of the filter and an upper lateral surface of the bend of the skeleton is to press against a wall of the first blood vessel. In some embodiments, the skeleton and the bows are made of a continuous wire. In some embodiments, the skeleton and the bows are made of an upper loop and a lower loop, and the mesh is held between the upper loop and the lower loop. In some embodiments, the filter includes knitted fibers. In some embodiments, the filter expands in response to an outward pull by the skeleton. In some embodiments, the weave of the filter is affixed at an angle to the skeleton that is other than a right angle. In some embodiments, the filter is made of a sheet of material that has holes. In some embodiments, the holes are of a non-uniform density on the material.

In some embodiments, the filter includes fibers that run in a first direction, and fibers that run in a second direction, wherein some fibers extend from a first side of the skeleton to a second side of the skeleton and back to the first side. In some embodiments, one or more fibers in a filter may contain a medicament. In some embodiments, the skeleton of the filter may include or be included in the mesh of the filter. In some embodiments, the device may include a clasp to connect the device to a catheter, where the clasp can be rotated clockwise to rotate the catheter clockwise, and can be rotated counterclockwise to rotate the catheter counterclockwise.

In some embodiments, the invention may include a method of inserting a device into a first blood vessel to cover with a filter an opening of a second blood vessel, pressing a bow attached to a skeleton of the device against a wall of the first blood vessel, and pressing a bow attached to the skeleton to the second blood vessel. In some embodiments, the pressing of a first bow includes pressing the bow against a lateral surface of an ascending aorta, and pressing the second bow includes pressing the bow against a medial surface of a subclavean artery. In some embodiments, a method of the invention includes bending an end of the skeleton below a plain of the filter, and pressing an upper lateral surface of the bend of the skeleton against a second wall of the first blood vessel. In some embodiments, the bows may be made of a continuous wire. In some embodiments, the filter may be between an upper loop and a lower loop of the skeleton. In some embodiments, the total area covered by the filter may be expanded by an outward pull by the skeleton. In some embodiments, the filter may be attached to the skeleton by a weave of the filter affixed at an angle to the skeleton other than a right angle. In some embodiments, the filter may include a sheet of material into which may be bored holes. In some embodiments, a fiber of the filter or skeleton may include a lumen that contains a medicament. In some embodiments, a method may include linking a clasp of the device to a clasp of a catheter, by pressing the clasp of the device onto the clasp of the catheter. In some embodiments, the device may be rotated counter clockwise upon a counterclockwise rotation of the catheter.

BRIEF DESCRIPTION OF THE DRAWINGS

The subject matter regarded as the invention is particularly pointed out and distinctly claimed in the concluding portion of the specification. The invention, however, both as to organization and method of operation, together with features and advantages thereof, may best be understood by reference to the following detailed description when read with the accompanied drawings in which:

DETAILED DESCRIPTION OF THE PREFERRED EMBODIMENTS

In the following description, various embodiments of the invention will be described. For purposes of explanation, specific examples are set forth in order to provide a thorough understanding of at least one embodiment of the invention. However, it will also be apparent to one skilled in the art that other embodiments of the invention are not limited to the examples described herein. Furthermore, well-known features or processes may be omitted or simplified in order not to obscure embodiments of the invention described herein.

Figure 1A:
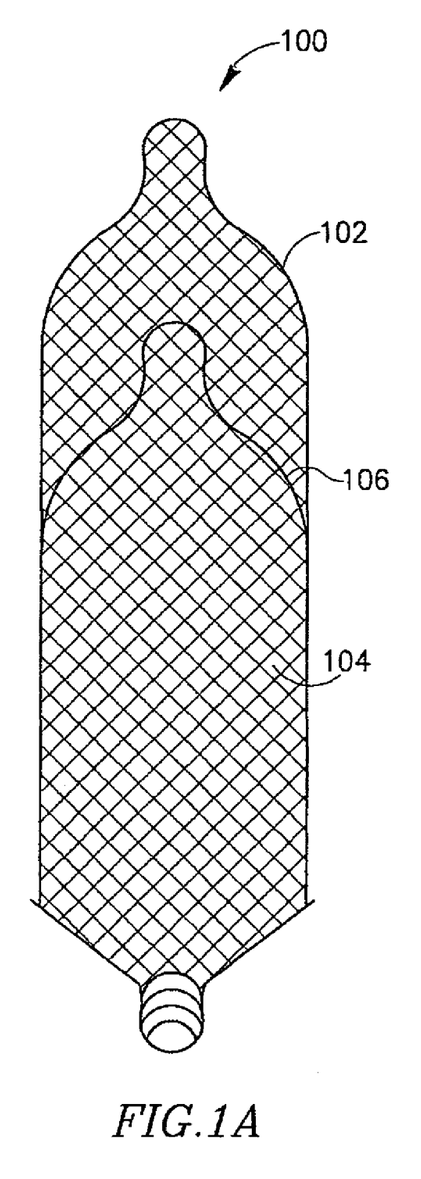
FIG. 1A is a schematic diagram of a front-view and FIG. 1B is a side-view of an intra-vascular device in accordance with an embodiment of the invention.
Figure 1B:
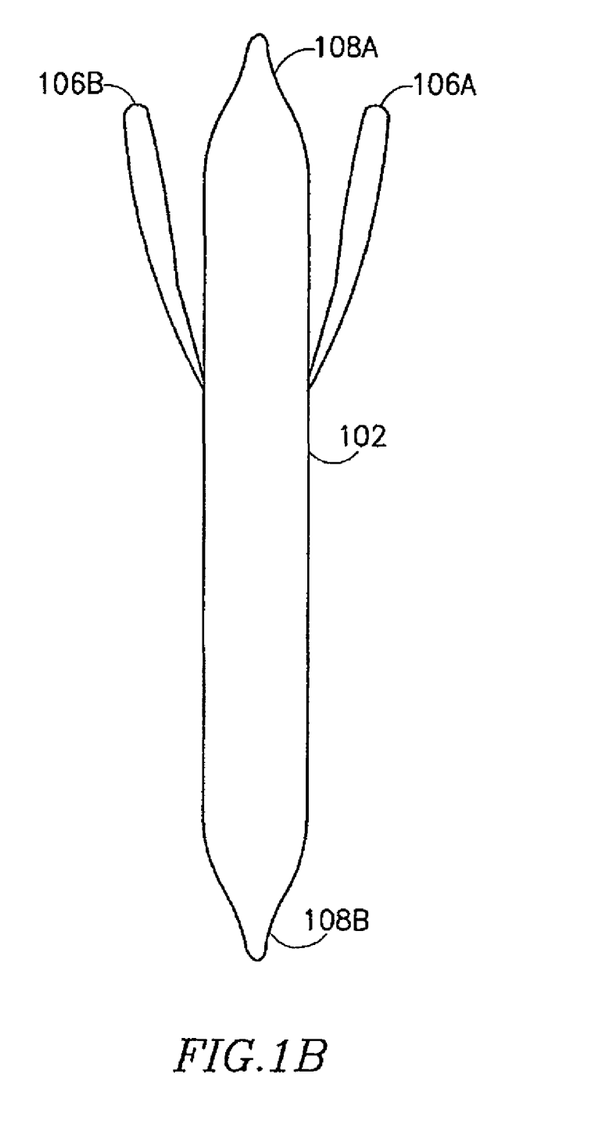

Reference is made to FIG. 1A, a schematic diagram of a front-view of a vascular filter, and to FIG. 1B, a schematic diagram of a side-view of a vascular filter in accordance with an embodiment of the invention. In some embodiments, an intra-vascular device (IVD) 100 may include a frame or skeleton 102, a filter 104 that may for example be held or supported by skeleton 102 and one or more bows 106A and 106b that may extend outwards from a lateral or horizontal plain of the IVD 100. In some embodiments, IVD 100 and filter 104 may be inserted into for example a blood vessel, and may prevent the passage of, block or filter out particles, such as for example blood clots, embolisms or other objects that may damage a blood vessel into which such particles may lodge. In some embodiments, IVD 100 may be inserted into a vessel by way of for example a catheter, and may be threaded into for example a blood vessel into which IVD 100 may be implanted. Other methods of implanting IVD 100 into a blood vessel are possible. In some embodiments, IVD 100 may assume a shape of an extended oval or of a willow leaf. Other shapes may be used.

One or more ends 108A and 108B of IVD 100 may be thinner or narrower than the rest of IVD 100. In some embodiments, an end 108 may terminate in a rounded knob shape, so that for example IVD 100 narrows but does not terminate in a point.

In some embodiments, skeleton 102 may include or be constructed of for example Nitinol or other superelastic or shape memory alloy or material. Other materials may be used. In some embodiments, filter 104 may be or include a fine wire netting or mesh, such as a mesh having holes or eyes of 300 microns or less such that for example particles that are larger than 300 microns are prevented from passing through the filter. Other sizes of holes or eyes may be used. In some embodiments, a shape of filter 104 may be defined or supported by a shape of skeleton 102.

In some embodiments, skeleton 102 may be part of filter 104. For example, skeleton may be or include a fiber of a mesh filter 104, that may in some embodiments define a shape of filter 104.

Figure 2:
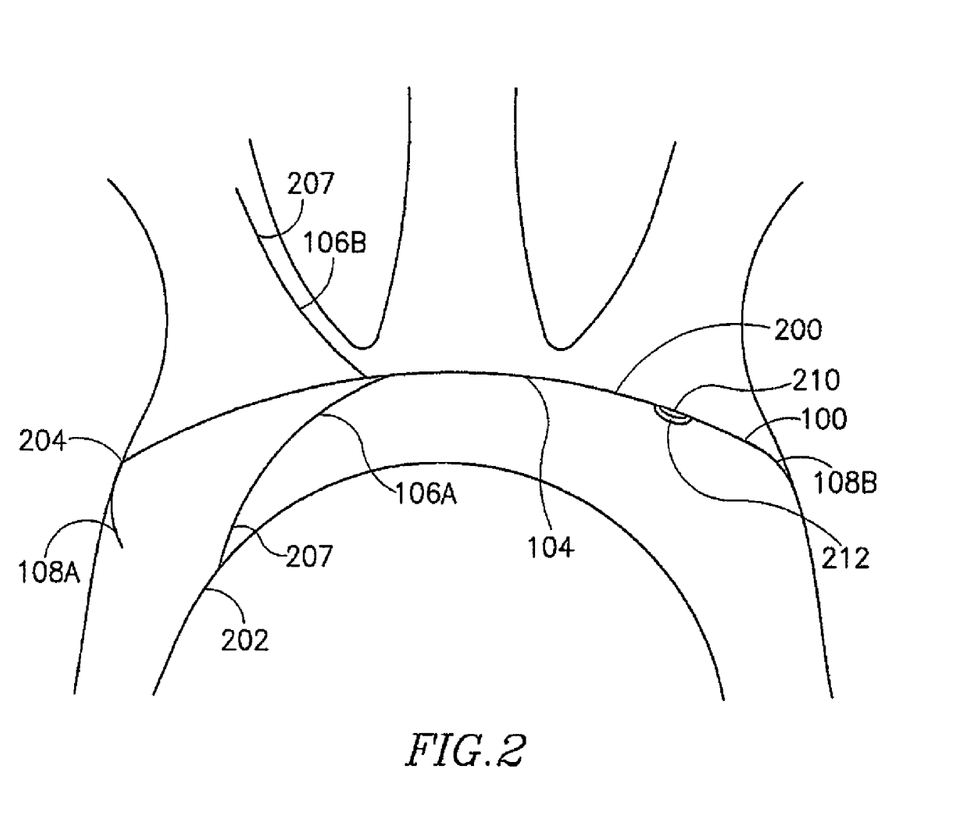
FIG. 2 is a view of an intra-vascular device implanted in a blood vessel in accordance with an embodiment of the invention. The device as depicted is substantially planar and bends approximately parallel to the aortic arch.

Reference is made to FIG. 2, a schematic illustration of an IVD 100 implanted into an aorta in accordance with an embodiment of the invention. In some embodiments, IVD 100 may be threaded by for example a catheter into an aorta or other vessel. IVD 100 may be implanted so that its lateral plain 200 extends from an area near or touching a medial wall of the ascending aorta 202 to an area near or touching a medial wall of a descending aorta. Other implant positions are possible IVD 100 may be situated in the lumen of an aorta but not covering the orifices of the vascular branches. In a preferred embodiment, filter 104 may be parallel to or at another angle to, and may cover one or more of an opening of a right subclavian, right common carotid, left common carotid, left subclavian arteries or other blood vessels. In some embodiments, filtering particles from entering such arteries may prevent particles from entering a brain of a patient, and may direct particles to a lower portion of a body where such particles may be less damaging.

In some embodiments one or more ends 108A and 108B of IVD 100 may upon installation or implanting in a vessel or at some other time, bend downwards from a lateral plain of the rest of IVD 100. In some embodiments such curve or downward bend may prevent an end 108 of IDV 100 from poking, injuring or otherwise damaging a wall of an artery and may allow end 108A and 108B to be held in place in contact with a lateral wall of an ascending aorta and concurrently in contact with an descending aorta, while lateral plain 200 of IVD 100 is situated in the lumen of an aorta but away from the orifices of the vascular branches. In some embodiments, an upper lateral side 204 or surface of IDV 100 or skeleton 102 may press up against for example an artery wall, such as for example a lateral wall of an ascending aorta and descending aorta, and such pressure may assist in keeping DV 100 in place away from the orifices of the vascular branches.

In some embodiments, IDV 100 may be implanted so that lower bow 106A extends past a curve (relative to a horizontal plain of IDV 100) of for example an ascending aorta 202, so that a surface such as a lateral surface 207 of bow 106A presses against or is in contact with a surface of for example a medial wall of for example the ascending aorta 202 and so that a surface such as a lateral surface 207 of upper bow 106B extends past a curve of an inlet into for example a subclavean artery, and presses against or is in contact with for example a medial wall of a subclavean artery. Such implanting and pressure from bows 106 may assist in keeping IDV 100 in place. Other positions for implanting IDV 100 and for placing bows 106 are possible.

In some embodiments, a bend of and end 108 of IDV 100 may have a radius of 25 mm, and may begin to bend from a lateral plain of IDV 100 approximately 15 mm before a tip of end 108. Other dimensions, arcs and radii may be used.

In some embodiments, filter 104 may include an opening 212 that may under normal conditions be covered by a flap 210. In some embodiments, flap 210 may be opened or pushed aside by for example an instrument such as for example a catheter to for example provide access to an area that is behind IVD 100.

Figure 3:
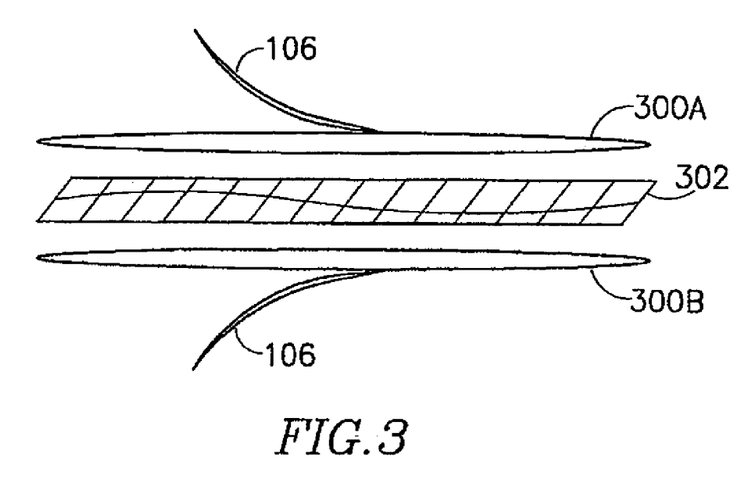
FIG. 3 is a schematic illustration of a construction of an intra-vascular device in accordance with an embodiment of the invention.

Reference is made to FIG. 3, a schematic illustration of a construction of an intra-vascular device in accordance with an embodiment of the invention. In some embodiments, a skeleton 102 of IVD 100 may be constructed of for example two or more parts, such as for example two or more loops 300A and 300B, and for example a mesh 302 that may be sandwiched between the two or more loops 300. In some embodiments, the two or more loops 300 may include bows 106. In some embodiments, when for example IVD 100 is constructed or at some other time, the two or more loops 300 such as an upper loop and a lower loop may be brought together and affixed on opposite sides of mesh 302. The loops 300 and mesh 302 may be glued, soldered or otherwise combined to form a single unit.

Figure 4:
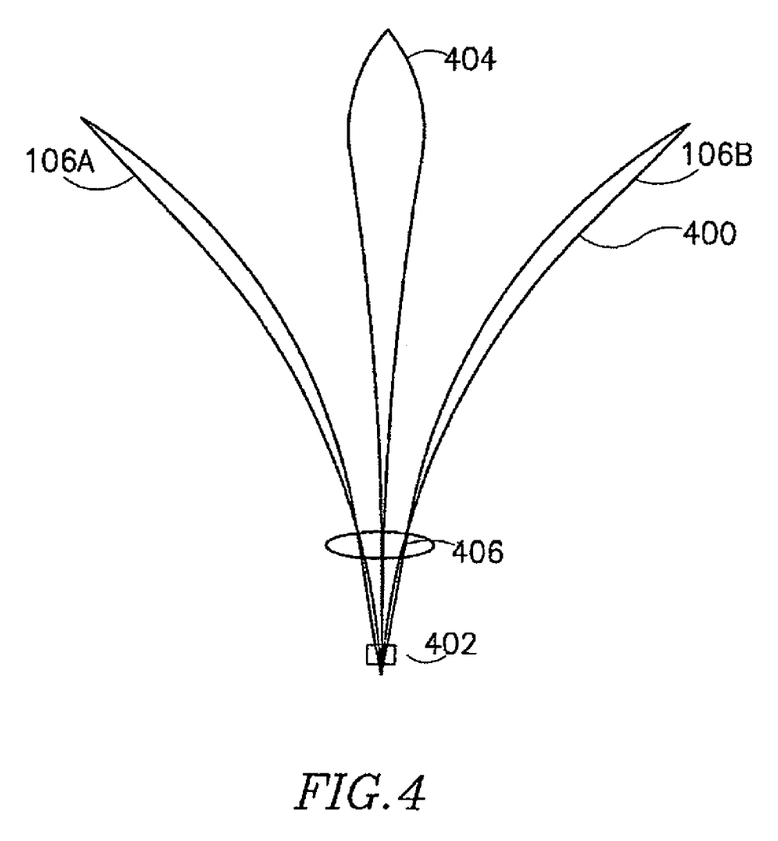
FIG. 4 is a schematic illustration of an intra-vascular device having a continuous wire construction in accordance with an embodiment of the invention.

Reference is made to FIG. 4, a schematic illustration of an intra-vascular device having a continuous wire construction in accordance with an embodiment of the invention. In some embodiments, a skeleton 102 of IVD 100 may include or be constructed of a shape retaining alloy such as for example Nitinol or other materials. In some examples, to avoid a complication or other adverse effect of connecting or bonding ends or other portions of a wire, filament or other segment of a shape retaining alloy, skeleton 102 of IDV 100 may be constructed of for example a continuous wire 400 or filament. For example, and in some embodiments skeleton 102 and bows 106 may be made of a single, continuous wire. For example, a first end of wire 400 may begin at for example a base 402 of IDV 100 and may extend upward and down again towards base 402 to create bow 106A, wire 400 may be extended back upward and downward again to create bow 106B, and then upward and back down a third time to create the shape 404 that supports filter 104. In some embodiments, base 402 may include or be constructed of for example a clasp or clamp that may hold or tie together the loops of wire 400. In some embodiments a ring 406 may hold some or all of the loops of wire 400 at a point for example before bows 106 angle away from a plain of IDV 100. In some embodiments a glue or other adhesive may hold the loops together. Other methods of holding wire 400 in a particular configuration are possible.

Figure 5:
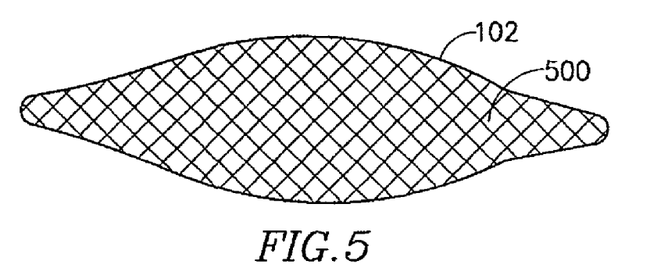
FIG. 5 is a schematic illustration of an intra-vascular device having fibers set at a non-right angle to a skeleton of a device in accordance with an embodiment of the invention.

Reference is made to FIG. 5, a schematic illustration of an intra-vascular device having fibers set at a non-right angle to a skeleton of a device in accordance with an embodiment of the invention. In some embodiments, a filter or mesh 500 may be configured from woven fibers 500 and is affixed to skeleton 102 so that its yarn orientation is at angles that are not right angles to skeleton 102. For example, in some embodiments, mesh 500 may be affixed to skeleton 102 so that the weave (warp and weft) of mesh 500 may be at for example 45° angles from a base or lateral portion of skeleton 102. When set at a non-right angle to skeleton 102, mesh 500 may stretch, expand or contract with greater flexibility than when such weave is at right angles to skeleton 102. In particular, such flexibility or capacity to contract may be beneficial in reducing a volume occupied by mesh 500 when the IVD 100 is folded or rolled into a catheter. Other methods of reducing a volume of rolled or folded mesh 500 are possible.

Figure 6:
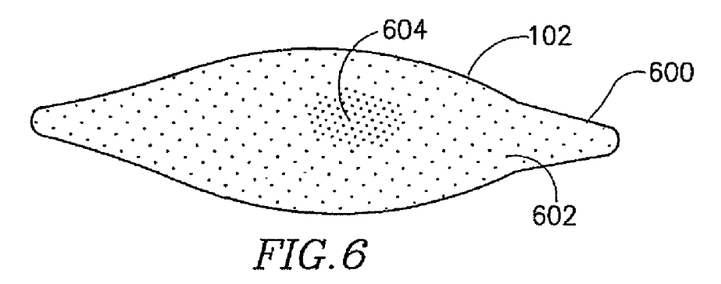
FIG. 6 is a schematic illustration of a sheet having varying hole densities serving as a filter in accordance with an embodiment of the invention.

Reference is made to FIG. 6, a schematic illustration of a mesh that may have been converted from a foil, film or sheet, having varying hole densities serving as a filter in accordance with an embodiment of the invention. In some embodiments, in addition to or in place of a mesh 500, a filter 600 may be constructed or for example, a sheet, curtain or continuous material that may be supported by for example skeleton 102, and that may have drilled into it or punctured through it, holes 602 or eyes of various sizes and densities. For example, in some embodiments, a flow of blood at or near a center 604 or center line of IVD 100 may be anticipated to be stronger than a flow of blood at or near an edge of IVD 100. The center 604 may therefore be fitted with more, less, smaller or larger or varying or non-uniform holes 602 than is an area of IVD 100 that is away from center 604. The pattern of holes, their distribution and dimension may be fitted to also control the flow characteristics of for example blood or other fluids around or near the filter 600. Such characteristics may include for example turbulence, vortexes and sheer stress forces. The film filter 600 may be constructed of or include a variety of polymers such as polyurethane, silicone, Teflon, polester and Pursil. The film filter 600 may be affixed to the skeleton by for example an adhesive or it may be welded using for example laser, radio frequency or ultrasonic waves. The film filter may also be formed directly over the skeleton by dipping the skeleton into a resin or liquid polymeric solution. Further, more than one layer of film filter 600 may be stretched or straightened over the skeleton, for example one filter from each side, and welded or adhered together to envelope the skeleton. Similarly, the film filter may be stretched and straightened on one side of the skeleton and folded over the other side to create for example a double layered film on some or all of the skeleton.

Figure 7:
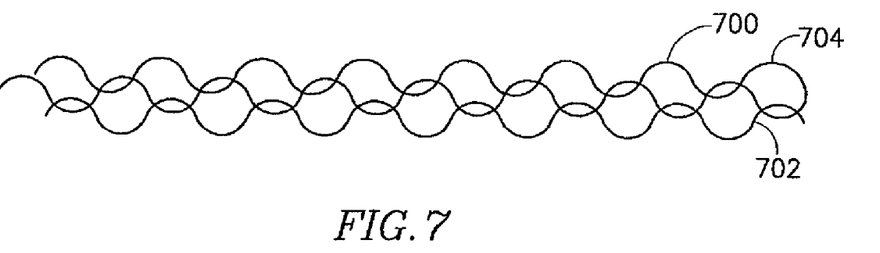
FIG. 7 is a schematic illustration of knitted filter fibers in accordance with an embodiment of the invention.

Reference is made to FIG. 7, a schematic illustration of a knitted filter material in accordance with an embodiment of the invention. In some embodiments, a mesh 700 of a filter may include fibers 702 that are knitted rather than or in addition to fibers that are criss-crossed at for example right angles to each other. In some embodiments, unlike a woven mesh, which may include horizontal or parallel courses of fibers, the fibers of a knitted mesh 700 may take a looping path such that interlocking loops of fibers are joined to each other where for example a short loop of one course of fiber is wrapped over the bight of another course of fiber. Other knitting stitches are possible. In some embodiments, fibers 702 in a knitted mesh 700 may intersect loosely rather than rigidly such that one or more fibers 702 may move or change a position relative to a position of another fiber 702. In some embodiments, one or more fibers 702 may not be rigidly attached to skeleton 102, but may rather be looped around skeleton 102 and may continue as part of the mesh 700 after such loop around skeleton 102. In some embodiments, the 'give' or flexibility of a knitted mesh 700 may allow the total area of mesh 700 to expand or contract depending on the forces, such as for example an outward pull exerted on fibers 702 by skeleton 704. For example, when IVD 100 may be folded inside for example a catheter, a total area of mesh 700 may be smaller than when skeleton 704 may be released from a catheter and may expand to its full state.

Figure 8:
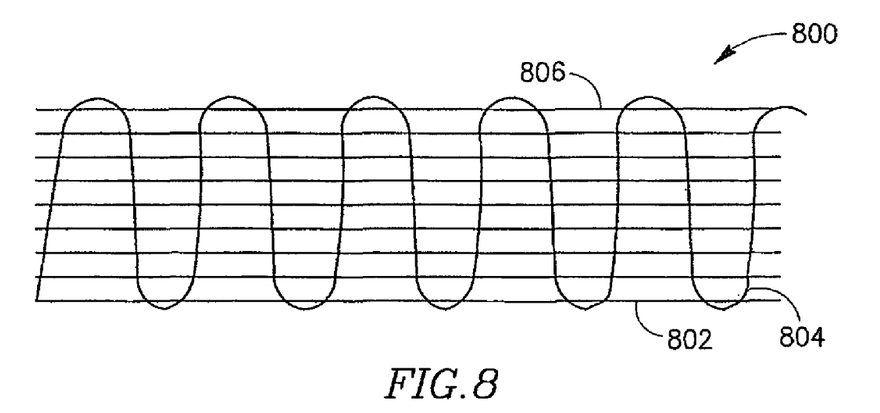
FIG. 8 is a schematic diagram of a partially knitted filter material in accordance with an embodiment of the invention.

Reference is made to FIG. 8, a schematic diagram of a partially knitted filter material in accordance with an embodiment of the invention. In some embodiments, a mesh 800 of IVD 100 may include a set of fibers 802 that are for example parallel to each other, and that may be affixed to for example skeleton 102, and one or more fibers that be woven over and under the parallel fibers and may run back and forth between a first side 804 of the skeleton 102 and a second side 806 of the skeleton 102, but that may not be affixed to skeleton 102. A weave of mesh 800 that includes one or more continuous fibers that runs back and forth between sides of IVD 100 may provide flexibility to the mesh 800.

In some embodiments, one or more of fibers 802 may include a lumen, such as for example a hollow fiber 802, which may hold for example a medicament that may be released into an artery or area where IVD 100 is implanted.

Figure 9A:
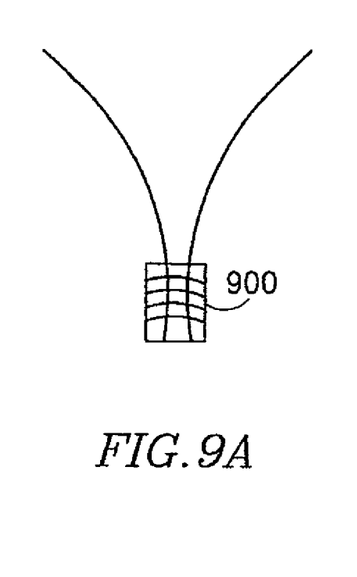
FIGS. 9A and FIG. 9B are illustrations of coupling devices of an intra-vascular device in accordance with an embodiment of the invention.
Figure 9B:
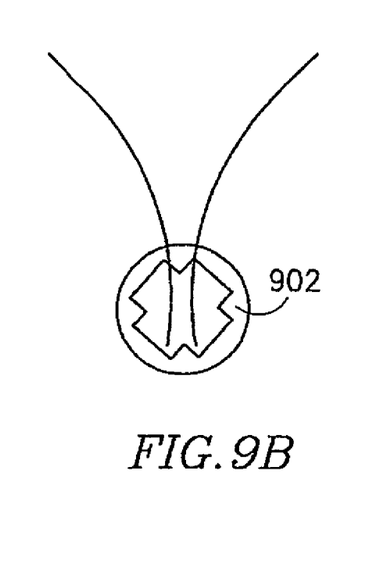

Reference is made to FIGS. 9A and 9B, illustrations of coupling devices of an intra-vascular device in accordance with an embodiment of the invention. In some embodiments, a coupling or clasping device may be located at a base of IVD 100, and may include a threaded male screw 900 onto which may be wound a female threaded joiner that may be for example attached to a delivery cable or catheter 906. In some embodiments, a clasp 902 may include a combination of releasable male clasp 902-female clasp 904, where one end of the clasp is on IVD 100 and another end on a catheter 906. A releasable clasp 904 may afford a coupling of IVD 100 to a catheter from many angles of the IVD 100 relative to the catheter, and from many angles of the male clasp 902 relative to the female clasp 904. The clasps may be joined by pressing the male clasp 902 into the female clasp 904, and as so joined, the IVD 100 may be rotated clockwise or counter-clockwise upon the clockwise or counterclockwise rotation of a catheter 906.

Figure 10:
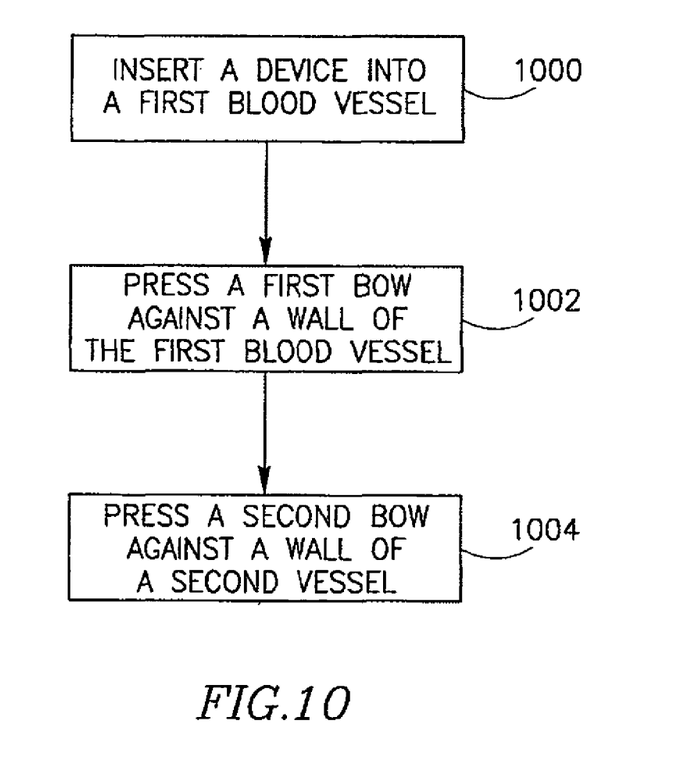
FIG. 10 is a flow diagram of a method in accordance with an embodiment of the invention.

Reference is made to FIG. 10, a flow diagram of a method in accordance with an embodiment of the invention. In block 1000, an intra vascular device may be inserted into a first blood vessel. In some embodiments, such first blood vessel may be or include an aorta, though the device may be inserted into other vessels. A filter of the device may be positioned so that an opening of a second blood vessel is covered by the filter, so that for example particles are filtered or prevented by such filter from entering into the second blood vessel. In some embodiments, a second blood vessel may include all or some of a subclavean artery, a carotid artery or other arteries. In block 1002, a first of two or more bows that may be attached to the device may be pressed against a wall of the first blood vessel, and the device may be held in place by such pressing of the bow against the wall. For example, in some embodiments, a lower surface of the first or lower bow may press against a medial wall of an ascending artery and the device may be prevented from moving up the aorta. In block 1004, an upper bow that may be attached to the skeleton of the device may press against a wall of a second blood vessel. In some embodiments, the second bow may press against for example an opening or bend of a subclavean artery. Other numbers of bows may be used and other surfaces or walls of arteries may be used.

In some embodiments, one or more ends of the device may bend or be bent downwards from or below a lateral plain of the filter and a lateral surface of the bent portion of the skeleton may press against a wall of a blood vessel. In some embodiments, the bent portion of the skeleton may press against for example a lateral wall of an ascending aorta.

In some embodiments, the skeleton and one or more of the bows may be constructed of a continuous wire. In some embodiments, the device may be constructed of two loops such as for example an upper loop and a lower loop, and a mesh may be sandwiched between the two loops of the skeleton.

In some embodiments, the total area of a mesh or filter may be contracted when the filter is folded up, and the total area of the filter may expand when the filter is unfolded. In some embodiments, a filter may be attached to the skeleton so that the weave of the filter is at an angle to the skeleton that is other than a right angle. In some embodiments, the angle of the weave or of the fibers may be for example 45° to the skeleton. In some embodiments, the fibers of the filter may be knitted rather than woven so that when the filter is pulled or expanded, a position of a fiber may be changed relative to a position of another fiber. In some embodiments, a fiber may be configured with a lumen running through its middle, and a medicament that may be stored in such lumen may be released inside of the blood vessel.

In some embodiments, a filter may be created by boring holes in a sheet, and in some embodiments the size and density of the holes may vary or be of non-uniform size or density depending on the location of the holes relative to the skeleton.

In some embodiments, a clasp at an end of the device may be pressed onto or into a clasp at for example an end of a catheter and the two clasps may be joined by such pressing. In some embodiments, the device may be rotated clockwise or counterclockwise when the catheter is rotated clockwise or counter-clockwise respectively.

It will be appreciated by persons skilled in the art that embodiments of the invention are not limited by what has been particularly shown and described hereinabove. Rather the scope of at least one embodiment of the invention is defined by the claims below.

We claim:

1. An intra-vascular device to prevent a particle in the aorta from passing into a second blood vessel, said device comprising:
   a filter
   a substantially planar frame to hold said filter; and
   a plurality of bows extending outwards from a horizontal plane of said frame, said plurality of bows comprising one or more bows configured to extend upward from the horizontal plane of said filter, and one or more bows configured to extend downward from the horizontal plane of said filter,
   wherein said frame defines the shape of said filter; wherein frame is suitable to the held in contact with both an ascending aorta and a descending aorta; wherein said one or more bows configured to extend upward is suitable to contact a medial surface of a subclavian artery; and wherein said one or more bows configured to extend downward is suitable to contact a medial surface of the ascending aorta.

2. The device as in claim 1, wherein said frame and said plurality of bows are comprised of a continuous wire.

3. The device as in claim 1, wherein said frame is comprised of an upper loop and lower loop, and a mesh, said mesh being held between said upper loop and said lower loop.

4. The device as in claim 1, said filter having a plurality of woven fibers.

5. The device as in claim 1, wherein an area of said filter expands in response to an outward pull by said frame.

6. The device as in claim 1, wherein a weave of said filter is affixed at an angle to said frame other than a right angle.

7. The device as in claim 1, wherein said filter comprises a sheet of material having holes.

8. The device as in claim 7, wherein said holes are of a non-uniform density on said material.

9. The device as in claim 1, wherein said filter comprises fibers, said fibers comprising a first plurality of fibers running in a first direction, and second plurality of fibers running in a second direction, wherein a fiber in said first plurality of fibers extends from a first side of said frame to a second side of said frame and back to said first side.

10. The device as in claim 9, wherein a fiber of said filter comprises a lumen, said lumen containing a medicament.

11. The device as in claim 1, wherein said filter comprises a mesh, and wherein said frame is comprised of said mesh.

12. The device as in claim 1, comprising a clasp to connect said device to a delivery cable, and wherein upon said connection, said device is rotated clockwise upon a clockwise rotation of said delivery cable, and is rotated counterclockwise upon a counterclockwise rotation of said delivery cable.

13. A method of preventing passage of a particle from an aorta into a subclavian artery comprising deploying the device of claim 1 in said aorta such that:
   (i) said one or more bows configured to extend downward of said deployed device contacts a medial surface of the ascending aorta;
   (ii) said one or more bows configured to extend upward of said deployed device contacts a medial surface of a subclavian artery;
   (iii) said frame of said deployed device contacts both the ascending aorta and descending aorta;

wherein said contacting holds said filter in the lumen of said aorta away from the orifices of vascular branches of said aorta; and wherein said deployment of said device prevents passage of particles from said aorta into said subclavian artery.

14. The method as in claim 13, further comprising: bending an end of said frame below a plane of said filter, and pressing an upper lateral surface of said bend of said frame against a second wall of said aorta.

15. The method as in claim 13, wherein said plurality of said bows and said frame are comprised of a continuous wire.

16. The method as in claim 13, comprising securing said filter between an upper loop and a lower loop of said frame.

17. The method as in claim 13, comprising expanding a total area of said filter upon an outward pull by said frame.

18. The method as in claim 13, comprising attaching said filter to said frame wherein a weave of said filter is affixed at an angle to said frame other than a right angle.

19. The method as in claim 13, comprising boring holes in a sheet of material comprising said filter.

20. The method as in claim 19, wherein said boring comprises boring said holes at a non-uniform density.

21. The method as in claim 13, comprising extending a plurality of woven fibers of said filter.

22. The method as in claim 13, comprising releasing a medicament from a lumen of a fiber of said filter.

23. The method as in claim 13, comprising linking a clasp of said device to a clasp of a catheter, by pressing said clasp of said device onto said clasp of said catheter.

24. The method as in claim 23, comprising rotating said device counterclockwise upon a counterclockwise rotation of said catheter.

25. The device as in claim 1, wherein said frame is suitable to be held in a lumen of said aorta away from orifices of vascular branches of said aorta.

\* \* \* \* \*